US006734188B1

(12) United States Patent
Rhodes et al.

(10) Patent No.: US 6,734,188 B1
(45) Date of Patent: May 11, 2004

(54) COMPOSITION FOR TREATMENT OF CONSTIPATION AND IRRITABLE BOWEL SYNDROME

(75) Inventors: John Rhodes, 25 Nant Fawr Road, Cyncoed, Cardiff, South Glamorgan (GB), CF2 6JG; Brian Kenneth Evans, 9 Merevale, St. Andrews Road, Dinas Powis, South Glamorgan (GB), CF6 4HS

(73) Assignees: John Rhodes, Glamorgan (GB); Brian Kenneth Evans, Glamorgan (GB)

( * ) Notice: Subject to any disclaimer, the term of this patent is extended or adjusted under 35 U.S.C. 154(b) by 0 days.

(21) Appl. No.: 10/111,850

(22) PCT Filed: Oct. 30, 2000

(86) PCT No.: PCT/GB00/04167
§ 371 (c)(1),
(2), (4) Date: Aug. 5, 2002

(87) PCT Pub. No.: WO01/32180
PCT Pub. Date: May 10, 2001

(30) Foreign Application Priority Data

Nov. 1, 1999 (GB) .............................................. 9925872
Nov. 30, 1999 (GB) .............................................. 9928314

(51) Int. Cl.$^7$ .......................... A61K 31/44; A61K 9/64; A61K 9/52; A61K 9/48

(52) U.S. Cl. ........................ 514/282; 424/456; 424/457; 424/463

(58) Field of Search .......................... 514/282; 424/456, 424/457, 463

(56) References Cited

U.S. PATENT DOCUMENTS

| 4,774,230 A | 9/1988 | Tuttle et al. |
| 4,987,136 A | 1/1991 | Kreek et al. |

FOREIGN PATENT DOCUMENTS

| EP | 0 647 448 A1 | 4/1995 |
| WO | WO 83/03197 | 9/1983 |
| WO | WO 99/22737 | 5/1999 |
| WO | WO 00/03660 | 1/2000 |
| WO | WO 01/32180 A2 | 5/2001 |

OTHER PUBLICATIONS

NP Sykes; Palliative Medicine, 1996, vol. 10, pp. 135–144.

*Primary Examiner*—Raymond J. Henley, III
(74) *Attorney, Agent, or Firm*—Birch, Stewart, Kolasch & Birch, LLP

(57) ABSTRACT

Constipation and Irritable Bowel Syndrome are treated by a delayed and sustained release composition of an opioid antagonist which commences release of the opioid antagonist in the mid to distal small intestine or ascending colon and provides sustained release along any remaining part of the small intestine and along the colon. Preferred opioid antagonists are naloxone and naltrexone.

22 Claims, No Drawings

COMPOSITION FOR TREATMENT OF CONSTIPATION AND IRRITABLE BOWEL SYNDROME

This application is a national stage application based on PCT/GB00/04167, filed Oct. 30, 2000, claiming priority of GB applications 9925872.5, filed Nov. 1, 1999, and 9928314.5, filed Nov. 30, 1999.

The present invention relates to the use of an opioid antagonist, especially naloxone and naltrexone, for the treatment of opioid induced or idiopathic constipation or of Irritable Bowel Syndrome (IBS) by delayed and sustained release.

Opioids, including codeine phosphate and morphine, are widely used as analgesics and are known to cause constipation as a troublesome and often serious complication. The effect is particularly troublesome amongst in-patients requiring prolonged opioid therapy in high doses such as terminally ill patients with a malignant disease. Treatment of the constipation is usually by use of conventional laxatives, but it is often poorly controlled.

IBS is a functional bowel disorder consisting of abdominal pain and altered bowel habit. Pain is characteristically relieved by defecation and may be associated with increase or decrease in stool frequency, alterations in stool consistency, straining or urgency, a sensation of incomplete evacuation, passage of mucus or abdominal distention. The pathophysiology is poorly understood despite the fact that about a quarter of the population in the UK may exhibit the symptoms.

There has been no convincing evidence that any current drug regime is of proven benefit in the treatment of IBS. Primary treatment involves counselling and dietary modification. Drug therapy is considered to be beneficial if directed at individual symptoms. For diarrhoea predominant cases, anti-diarrhoeal drugs are used, particularly loperamide. For constipation predominant cases, ispaghula is often used to increase dietary fibre. Where patients have pain and distension as predominant symptoms, antispasmolytics are commonly used. Mebeverine and peppermint oil are often used in such cases. Other agents that have been tried, in treating IBS, include beta-blockers, naloxone, ondansetron, calcium channel blockers, simethicone, leuprorelin, octreotide and cholecystokinin antagonists, with variable results (Martindale The Extra Pharmacopoeia, 31st Edition (1996) p 1197).

Naloxone (17-allyl-6-deoxy-7,8-dihydro-14-hydroxy-6-oxonormorphine) is known to be a specific opioid antagonist and is given intravenously for the treatment of opioid-overdosage and to reverse therapeutic effects of opioids (for example postoperatively when opioids are used during surgery). It has a short plasma half-life of about 1 h after parenteral administration. It is absorbed from the gastrointestinal tract and subject to considerable first-pass metabolism.

Naltrexone (17-(cyclopropylmethyl)-4,5$_\alpha$-epoxy-3,14-dihydroxymorphinan-6-one) is known to have opioid-blocking activity. It is given orally in the treatment of opioid dependence as an aid to maintaining abstinence following opioid withdrawal. Naltrexone is more potent than naloxone and has a longer duration of action. Naltrexone is also used as an adjunct in the management of alcohol withdrawal.

Strong opioids delay gastrointestinal transit and patients treated with them experience marked constipation. The delay is partly mediated by opioid receptors in the gut. Naloxone has been shown to produce a laxative effect in patients with advanced cancer that are being treated with an opioid analgesic, although there were a number of instances of withdrawal observed. It appeared that the dose regime of naloxone was dependent on the dose of the constipation-causing opioid administered, however it was observed that any clinical use of naloxone should not depend on the dose being estimated based on a measured plasma concentration. Indeed, the dose of the opioid was not the only consideration. Patients that have been on longer term treatment of opioids and are thus more physically dependent appear to be more sensitive to naloxone treatment and show more withdrawal symptoms (N. P. Sykes, *Palliative Medicine*, 1996, 10, 135).

It has been suggested (N. P. Sykes, *Palliative Medicine*, 1996, 10, 135) that oral naloxone might have a therapeutic role in treatment of opioid induced constipation and that a slow release formulation could offer 12 or 24 hour administration, although it has been conceded that this would increase the difficulty of reversing any withdrawal that occurred.

WO 99/22737 (Drell et al) discloses a method for treating or preventing a range of conditions, often side effects from the use of opioid analgesics, including both opioid induced and non opioid induced constipation by administering a quaternary derivative of noroxymorphine, especially methylnaltrexone. The noroxymorphine derivative may be enterically coated to delay the release of the drug. Systemic uptake is not totally avoided, but quaternary ammonium salts such as methylnaltrexone do not cross the blood-brain barrier to a significant extent thus minimising the reduction of any opioid induced analgesic effect.

U.S. Pat. No. 4,774,230 (Tuttle et al) relates to the intestine specific delivery of opioid antagonists including naloxone and naltrexone for treating opioid induced and idiopathic constipation and IBS. The drug is targeted to the intestine by virtue of an inactive glucoronic acid derivative which is enzymatically cleaved by glucoronidase, in the lower intestine and particularly the colon. The glucoronic acid derivative may be in the form of capsules or tablets for oral administration and may have enteric coatings such as polyacrylates or cellulose acetate phthalates.

U.S. Pat. No. 4,987,136 (Kreek et al) relates to the treatment of a range of gastrointestinal dysmotility conditions including constipation and IBS by administering opioid antagonists such as naloxone or naltrexone. Preferably, the opioid antagonist will be in an oral sustained release form allowing sustained release along the gastrointestinal tract, in a pH independent manner. The sustained release formulation may be administered in a hard gelatin capsule.

There is a need to provide a therapeutic treatment that will relieve (opioid induced) constipation and treat IBS. The desired therapy would relieve opioid induced constipation without reversing the analgesic effect for which the opioid was intended.

The inventors have now found that an opioid antagonist specifically released, initially, in the mid to distal small intestine, especially the distal ileum, and/or ascending colon is effective in treating IBS and both opioid induced and idiopathic constipation.

Accordingly, in a first aspect of the invention, there is provided an opioid antagonist for use in the manufacture of a medicament for the treatment of a condition selected from constipation and Irritable Bowel Syndrome by targeting initial release of said antagonist to the mid to distal small intestine and/or ascending colon and providing subsequent sustained release of said antagonist along any remaining part of the small intestine and along the colon.

Preferably, initial release of the antagonist is targeted to the distal ileum and/or ascending colon and subsequent sustained release occurs along the colon.

The invention has particular application to the treatment of idiopathic constipation and especially opioid induced constipation.

Preferred opioid antagonists for use in the invention are naloxone and naltrexone and pharmacologically acceptable salts, derivatives and metabolites thereof.

Other opioid antagonists include methyl naloxone, nalmefene, cypridime, beta funaltrexamine, naloxonazine, naltrindole, nor-binaltorphimine and any pharmacologically acceptable salts, derivatives and metabolites thereof.

References herein to pharmacologically acceptable derivative, include any derivative which has the same type of pharmacological activity as the relevant opioid antagonist.

In a second aspect of the invention, there is provided a composition comprising an opioid antagonist in an oral delayed and sustained release form which targets initial release of the opioid antagonist to the mid to distal small intestine and/or ascending colon and provides sustained release along any remaining part of the small intestine and along the colon.

Preferably, initial release of the antagonist is targeted to the distal ileum and/or ascending colon and subsequent sustained release occurs along the colon.

The presently preferred opioid antagonist is naloxone. This substance is particularly suited to administration by the oral route since it is known to be efficiently metabolised by the liver, which minimises its absorption into the blood circulatory system thus limiting the risk of systemic side effects, such as negation of systemic pain relief for which certain opioids are administered.

The delayed release is preferably provided by having the composition in an enterically coated capsule which will not dissolve in the stomach but will allow initial release of the opioid antagonist in the mid to distal small intestine and/or ascending colon and preferably will allow initial release of the opioid antagonist in the distal ileum and/or ascending colon.

The sustained release is preferably provided by a composition which releases the opioid antagonist over a period of 3 to 24 hours, more preferably 6 to 12 hours.

The composition preferably comprises an opioid antagonist dispersed in a matrix enclosed in a capsule which disintegrates upon reaching the mid to distal small intestine and/or ascending colon and preferably the distal ileum and/or ascending colon to allow subsequent sustained release of the opioid antagonist from the matrix.

The matrix may be a thermolabile matrix which begins to soften within the capsule as it moves along the gastrointestinal tract and releases the opioid antagonist over a sustained period.

The sustained release of the opioid antagonist can be achieved by use of a polyglycolised glyceride. The polyglycolised glyceride may be comprised of mono-, di- and triglycerides and of mono- and di- fatty acid esters of polyethylene glycol (PEG) and held in an enteric coated orally administrable capsule. The polyglycolised excipient acts as a particularly good matrix to release the opioid antagonist over a prolonged period. The enteric coating carries the capsule past the stomach to the mid to distal small intestine and/or ascending colon where it dissolves and the opioid antagonist is released along the target area over a period of hours. The polyglycolised glyceride can be adapted to have a different melting point and hydrophilic-lipophilic balance (HLB) depending on the type and proportion of triglyceride and fatty acid esters of PEG used. Examples of commercially available polyglycolised excipients for use in the composition are those available from Gattefosse, France under the Trade Mark Gelucire.

Such compositions are particularly effective in the treatment of opioid induced constipation without reversing the analgesic effects of the opioid, as well as idiopathic constipation.

In a particularly preferred delayed and sustained release oral composition, the opioid antagonist is suspended in a polyglycolised glyceride, preferably Gelucire™, more preferably Gelucire™ 50/13, that is Gelucire™ with a melting point of 50° C. and HLB value of 13, or Gelucire™ 42/12 and most preferably Gelucire™ 53/10 (providing about 12 h sustained release) or a matrix combination of Gelucire™ 50/13 and Gelucire™ 42/12 in the ratio 80:20 to 95:5 (providing 6 to 12, preferably 6 to 9 hours sustained release) especially in the ratio 82.5:17.5. The suspension is then dosed in a capsule and the capsule enteric coated.

An advantage of using a matrix, as described above, particularly the identified Gelucire™ combinations, in a composition for sustained release of an opioid antagonist is that there is a unique hydrophilic-lipophilic balance which allows the formation of an emulsion as the softening matrix travels along the intestine. It is believed that the physical characteristics of the matrix vehicle cause it to be located close to the gastrointestinal wall in transit and thus in close proximity to mucosa and local receptor sites. The combination of these features leads to improved exposure to receptor sites and a prolonged transit time.

Suitable enteric coating materials for use in the present invention include cellulose acetate phthalate (CAP), polyvinyl acetate phthalate (PVAP) and hydroxypropyl methylcellulose phthalate, although preferable enteric coatings are those polymers based on acrylic and methacrylic acid. A suitable such material is the anionic methacrylate polymer sold under the registered Trade Mark EUDRAGIT™ S by Rohm Pharma GmbH of Darmstadt, Germany. EUDRAGIT™ S is a copolymer of methacrylic acid and methyl methacrylate in which the ratio of free carboxyl groups to ester groups is approximately 1:2 and having a mean molecular weight of 135,000. Coatings of acidic materials, such as that sold as EUDRAGIT™ L (composition as EUDRAGIT™ S but having a carboxyl/ester ratio of 1:1) or EUDRAGIT™ S may be used in the coating of tablets or capsules. It will be apparent to the skilled person that mixtures of substances, such as EUDRAGIT™ S and EUDRAGIT™, may be used as coating materials. Particularly preferred enteric coatings in accordance with the invention are EUDRAGIT™ S and LS (e.g. in a L:S ratio of 1:2).

The provision of the coating to the compositions of the invention may be achieved in conventional manner, e.g. by the use of spraying, fluidized bed, immersion tube and immersion blade techniques.

The coating can, and usually will, contain plasticiser and possibly other coating additives such as colouring agents, gloss producers, talc and/or magnesium stearate as well known in the coating art. In particular, anionic carboxylic acrylic polymers usually contain 10 to 25% by weight of a plasticiser especially diethyl phthalate, although the presence of such a plasticiser may not be necessary when using an aqueous suspension for coating.

Usually, the capsule into which the coated material is loaded will be a soft or, preferably, hard gelatin capsule although other capsules, such as cellulose-based capsules, which will dissolve in the small intestine can be used.

A suitable unit dose for the treatment of constipation by opioid antagonists is in the range of 0.5 to 30 mg naloxone or the equivalent thereof.

The invention will now be illustrated by the following non-limiting Examples.

EXAMPLE 1

A delayed, sustained release oral formulation was prepared as follows. Naloxone hydrochloride (10 mg) was suspended in 400 to 450 mg of a matrix of Gelucire™ 50/13 and Gelucire™ 42/12 (a polyglycolised glyceride supplied by Gattefosse, France) in the ratio 82.5:17.5 and the resulting suspension filled into a size No. 2 hard gelatin capsule.

Formulations were also prepared with naloxone suspended in the following polyglycolised glycerides: a) Gelucire™ 42/12, b) Gelucire™ 44/14, c) Gelucire™ 46/07, d) Gelucire™ 48/09, e) Gelucire™ 50/13, f) Gelucire™ 53/10, g) Gelucire™ 54/02, h) Gelucire™ 62/05, i) Gelucire™ 64/02, j) Gelucire™ 54/02 & Gelucire™ 46/07 50:50, k) Gelucire™ 62/05 & Gelucire™ 46/07 50:50, l) Gelucire™ 64/02 & Gelucire™ 46/07 50:50, m) Gelucire™ 54/02 & Gelucire™ 46/07 75:25, n) Gelucire™ 64/07 & Gelucire™ 46/07 75:25, o) Gelucire™ 54/02 & Gelucire™ 46/07 30:70, p) Gelucire™ 64/02 & Gelucire™ 46/07 30:70, q) Gelucire™ 53/10 & Gelucire™ 42/12 92.5:7.5, r) Gelucire™ 50/13 & Gelucire™ 42/12 95:5, s) Gelucire™ 42/12, Gelucire™ 54/02 & Gelucire™ 46/07 5:45:50, t) Gelucire™ 42/12, Gelucire™ 64/02 & Gelucire™ 46/07 7.5:42.5:50 and u) Gelucire™ 53/10 & Gelucire™ 42/12 90:10.

The capsules were then enteric coated using a 3% w/w acrylic resin (Eudragit™ S) dissolved in an organic solvent mixture (methanol 10% v/v in acetone 90% v/v). Diethyl phthalate was included as the plasticiser and dimethicone as a lubricant. 75 cm³ of this mixture was used to coat 100 capsules.

12 healthy, non-smoking volunteers were enrolled in a study to assess the effect of oral naloxone when taking oral codeine.

The study consisted of four 10-day study periods, with at least two weeks between each, which were in a randomised order and the capsules being administered daily in a double blind manner. The capsules in each case were A (codeine phosphate 30 mg or placebo) and B (naloxone 10 mg or placebo) and the study conducted such that all four combinations of treatments were given, that is to say placebo only, codeine with placebo, placebo with naloxone and codeine with naloxone. The capsules were administered twice a day ("bd"). The naloxone formulation used was that in a matrix of Gelucire™ 50/13 and Gelucire™ 42/12 in the ratio 82.5:17.5.

The study protocol was as follows: On day 0, subjects were given capsule B and on days 1 to 9, were given capsules A and B. On days 3 to 6, the subjects took transit markers; packaged in distinctly coloured capsules, each containing 20 different shaped radio opaque marker pellets (Dunn Clinical Nutrition). From day 7, the subjects' next two bowel motions were collected. A normal diet was adhered to throughout the study period and recorded on days 3 to 6.

The results of the study are presented in tables of gut transit times. Table 1 shows the gut transit time of all 12 patients in the study for the control period and for the periods of treatment with codeine, naloxone and the combined treatment. Table 2 shows gut transit times for only those patients whose gut transit time was increased when taking codeine.

TABLE 1

Gut transit times of all patients (n = 12)

|  | Minimum (h) | Maximum (h) | Median (h) | Mean (h) | SEM[a] |
|---|---|---|---|---|---|
| Control period | 38.00 | 74.00 | 52.35 | 53.08 | 3.03 |
| Codeine 30 mg bd[b] | 25.22 | 84.00 | 56.76 | 57.27 | 5.18 |
| Naloxone 10 mg bd[b] | 27.40 | 63.91 | 38.85 | 42.13 | 3.69 |
| Combined therapy | 26.20 | 74.00 | 36.60 | 40.74 | 3.96 |

[a]SEM = Standard Error of the Mean;
[b]bd = twice a day

TABLE 2

Gut transit times of 8 patients whose transit time was increased by codeine (n = 8)

|  | Minimum (h) | Maximum (h) | Median (h) | Mean (h) | SEM[a] |
|---|---|---|---|---|---|
| Control period | 38.00 | 64.00 | 48.95 | 50.44 | 3.02 |
| Codeine 30 mg bd[b] | 50.42 | 84.00 | 67.85 | 66.17 | 4.21 |
| Naloxone 10 mg bd[b] | 27.40 | 63.91 | 37.95 | 41.41 | 5.08 |
| Combined therapy | 27.40 | 74.00 | 39.22 | 42.40 | 5.44 |

[a]SEM = Standard Error of the Mean;
[b]bd = twice a day

Statistical analysis of the above results was carried out and the results of this analysis are expressed as P values in Table 3.

The results appear to be a good approximation to a normal distribution. For the sake of clarity both parametric and non-parametric statistics have been performed.

TABLE 3

Significance of difference between groups of paired data

|  | Student's test | | Wilcoxon rank | |
|---|---|---|---|---|
|  | All patients | Codeine affected | All patients | Codeine affected |
| Control vs. codeine | 0.459 | 0.001 | 0.48 | 0.12 |
| Control vs. naloxone | 0.005 | 0.034 | 0.006 | 0.036 |
| Control vs. combined | 0.024 | 0.201 | 0.026 | 0.161 |
| Codeine vs. naloxone | 0.020 | 0.000 | 0.034 | 0.012 |
| Codeine vs. combined | 0.007 | 0.002 | 0.023 | 0.017 |

The experiment showed that naloxone alone and naloxone with codeine both produced reduced gut transit time. This indicates that the naloxone preparation accelerates gut transit by blocking opioid receptors and hence is effective in both opioid induced constipation and idiopathic constipation.

EXAMPLE 2

In a further study, the procedure of Example 1 was substantially followed using Gelucire™ 53/10 & Gelucire™ 42/12 95:5 as the polyglycolised glyceride matrix. The capsule was enterically coated with a mixture of acrylic resin materials (Eudragit™LS) which caused the capsule to remain intact until the mid small intestine. The glyceride provided a harder melt than Gelucire™ 50/13 & Gelucire™ 42/12 82.5:17.5 and released the naloxone over a 12 hour period.

12 male volunteers throughout each of four 10–14 day study periods were given a fixed dose of naloxone (5 mg bd, 10 mg bd, 20 mg bd or identical placebo). The gut transit time was measured at the end of the first week. During the second week, each volunteer was also given 30 mg bd codeine and gut transit times measured again at the end of the second week.

The outcome of the study was that naloxone in all three doses was shown to accelerate gut transit time by blocking the opioid effect, with the 10 and 20 mg bd doses being more reliable.

EXAMPLE 3

A 38 year old female patient with Irritable Bowel Syndrome having been subject to abdominal distension, pain and constipation for approximately ten years was treated with a naloxone hydrochloride formulation as used in Example 1, administered twice daily for one year. The treatment kept the patient almost symptom free for the duration of the treatment.

EXAMPLE 4

A 66 year old female patient demonstrating the symptoms of irritable bowel syndrome was administered, intermittently, with a similar dosage form of naloxone hydrochloride to that of example 3 and showed substantial clinical benefit.

What is claimed is:

1. A composition comprising an opioid antagonist in an oral delayed and sustained release form which targets initial release of the opioid antagonist to the mid to distal small intestine and/or ascending colon and provides sustained release along any remaining part of the small intestine and along the colon.

2. A composition as claimed in claim 1, wherein said opioid antagonist is naloxone or a pharmaceutically acceptable salt thereof.

3. A composition as claimed in claim 1, wherein said opioid antagonist is naltrexone or a pharmaceutically acceptable salt thereof.

4. A composition as claimed in claim 1, wherein the opioid antagonist is dispersed in a matrix enclosed in a capsule which capsule disintegrates upon reaching the mid to distal small intestine and/or ascending colon to allow subsequent sustained release of the opioid antagonist from the matrix.

5. A composition as claimed in claim 4, wherein said matrix is a thermolabile matrix.

6. A composition as claimed in claim 5, wherein said matrix comprises a saturated polyglycolized glyceride excipient selected from the group consisting of mono-, di- and triglycerides and mono- and dicarboxylic fatty acid esters of polyethylene glycol.

7. A composition as claimed in claim 5, wherein said matrix comprises a polyglycolized excipient having a melting point/HLB value of 53/10.

8. A composition as claimed in claim 5, wherein said matrix comprises a mixture of polyglycolized excipients having melting point/HLB values of 50/13 and 42/12.

9. A composition as claimed in claim 8, wherein said mixture of 50/13 and 42/12 excipients are present in a ratio in the range 80:20 to 95:5.

10. A composition as claimed in claim 4, which capsule is an enteric coated gelatin capsule.

11. A composition as claimed in claim 10, wherein the enteric coating comprises a copolymer of methacrylic acid and methyl methacrylate having a ratio of free hydroxyl groups to ester groups of 1:1 to 1:2.

12. A composition as claimed in claim 11, wherein the enteric coating comprises a copolymer of methacrylic acid and methyl methacrylate having a ratio of free hydroxyl groups to ester groups of 1:2.

13. A composition as claimed in claim 1, containing the opioid antagonist in an amount of 0.5 to 30 mg naloxone per unit dose.

14. A method for the treatment or prophylaxis of a condition selected from the group consisting of constipation and Irritable Bowel Syndrome comprising administering to a patient an effective amount of an oral delayed and sustained release composition comprising an opioid antagonist selected from the group consisting of naloxone, naltrexone and pharmaceutically acceptable salts thereof, which composition targets initial release of the opioid antagonist to the mid to distal small intestine and/or ascending colon and provides sustained release along any remaining part of the small intestine and along the colon.

15. A method for the treatment or prophylaxis of a condition selected from the group consisting of constipation and Irritable Bowel Syndrome comprising administering to a patient an effective amount of an opioid antagonist by targeting initial release of said antagonist to the mid to distal small intestine and/or ascending colon and providing subsequent sustained release of said antagonist along any remaining part of the small intestine and along the colon.

16. A method as claimed in claim 15, wherein the condition is constipation.

17. A method as claimed in claim 15, wherein the condition is Irritable Bowel Syndrome.

18. A method as claimed in claim 15, wherein said opioid antagonist is naloxone or a pharmaceutically acceptable salt thereof.

19. A method as claimed in claim 15, wherein said opioid antagonist is naltrexone or a pharmaceutically acceptable salt thereof.

20. A method as claimed in claim 16, wherein the constipation is opioid induced.

21. A method as claimed in claim 15, wherein the initial release of the opioid antagonist is targeted to the ascending colon.

22. A method as claimed in claim 15, wherein the initial release of the opioid antagonist is targeted to the distal ileum.

* * * * *